US006936041B2

(12) United States Patent
Viitala

(10) Patent No.: US 6,936,041 B2
(45) Date of Patent: Aug. 30, 2005

(54) REINFORCED VENOUS DRAINAGE CATHETER

(75) Inventor: Daniel W. Viitala, Dexter, MI (US)

(73) Assignee: Terumo Cardiovascular Systems Corp., Ann Arbor, MI (US)

( * ) Notice: Subject to any disclaimer, the term of this patent is extended or adjusted under 35 U.S.C. 154(b) by 33 days.

(21) Appl. No.: 10/252,050

(22) Filed: Sep. 23, 2002

(65) Prior Publication Data

US 2003/0078564 A1 Apr. 24, 2003

Related U.S. Application Data

(63) Continuation-in-part of application No. 09/978,699, filed on Oct. 18, 2001, now abandoned.

(51) Int. Cl.[7] ........................ A61M 25/00
(52) U.S. Cl. ........................ 604/525; 604/508
(58) Field of Search ........................ 604/27, 35, 43, 604/508, 514, 93.01, 158, 523–527, 264, 532; 600/433–435

(56) References Cited

U.S. PATENT DOCUMENTS 4,639,252 A 1/1987 Kelly et al.
5,769,828 A * 6/1998 Jonkman ........ 604/508
5,807,354 A 9/1998 Kenda
6,152,911 A * 11/2000 Giannoble ........ 604/524

FOREIGN PATENT DOCUMENTS

WO WO 99/37341 * 7/1999
WO WO 01/34237 5/2001

* cited by examiner

*Primary Examiner*—Nicholas D. Lucchesi
*Assistant Examiner*—Michael M. Thompson

(57) ABSTRACT

A venous catheter comprises a flexible plastic tubular body having a center lumen. A plurality of drainage openings are formed in a reinforced opening-containing section of the body. Reinforcement is embedded in the body within the reinforced opening-containing section. The reinforcement includes a series of annular ringlets each formed of a few tightly wound helical turns. The ringlets can be non-interconnected, or interconnected by a helical connecting part by forming the ringlets and connecting parts from a continuous wire. The drainage openings are disposed in spaces formed between successive ringlets.

15 Claims, 4 Drawing Sheets

14
18
18
20
23
27
26f
26m
24
26r
25
12
10
22

REINFORCED VENOUS DRAINAGE CATHETER

This is a Continuation-In-Part of U.S. Ser. No. 09/978,699, filed Oct. 18, 2001, now abandoned.

BACKGROUND OF THE INVENTION

This invention relates to venous drainage catheters, and especially to multi stage venous catheters.

A venous drainage catheter is used during cardiac surgery to remove blood from or near the patient's venous system. The removed blood is conducted to heart lung equipment which treats the blood, e.g., by removing carbon dioxide, infusing oxygen, heating, cooling, etc. before returning the treated blood to the patient.

The catheter includes drainage openings for conducting blood from the right atrium and/or vena cava.

During introduction of the catheter into the patient's body, or during subsequent adjustment of the catheter, the catheter may become bent, which tends to produce kinking that will undesirably reduce blood flow. Consequently, it is conventional to reinforce the catheter to prevent such bending.

For example, U.S. Pat. No. 4,639,252 discloses a catheter reinforcement in the form of a cylindrical plastic sleeve embedded in the plastic body of the catheter, with drainage openings punched through the body and sleeve.

In U.S. Pat. No. 5,769,828 a catheter reinforcement is disclosed which is comprised of axially extending beams spaced circumferentially apart. Alternating pairs of adjacent beams are interconnected at their forward or rearward ends by a circumferentially extending connecting piece. There is thus provided a reinforcement which is capable of being expanded over a larger diameter. Drainage holes are punched through the body of the catheter in spaces formed between adjacent beams.

Reinforcement for a catheter disclosed in U.S. Pat. No. 6,152,911 comprises a coil spring defining spaces between successive turns of the coil. Drainage openings are formed in those spaces.

Common to each of the above-described reinforced catheters is the creation of a uniform reinforcement along a section of the catheter. Although such uniform reinforcement resists the tendency for kinking to occur in that section, it also resists the bending of the catheter thereby considerably limiting the flexibility of the section.

It would be desirable to provide a venous drainage catheter with reinforcement which produces minimal resistance to bending thereof while effectively resisting kinking.

SUMMARY OF THE INVENTION

The present invention relates to a venous drainage catheter which comprises a flexible elongated tubular plastic body having distal and proximal ends and an interior lumen extending from the distal end to the proximal end along a longitudinal access of the body. The interior lumen has a plurality of longitudinally spaced drainage openings formed in a reinforced opening-containing section of the body. Each opening extends from the outside of the body to the interior lumen for providing fluid communication between the interior lumen and the exterior of the catheter. Reinforcement is embedded in the plastic body within the reinforced opening-containing section. The reinforcement comprises a plurality of annular elements oriented substantially perpendicularly to the longitudinal access of the body, wherein at least one of the drainage openings is disposed between and spaced from an adjacent pair of the annular elements. No portion of the reinforcement interconnects the annular elements.

Alternatively, the annular elements could be formed by a continuous wire which is wound a few turns to form each annular element and includes a connecting section extending helically from one annular element to the next.

The reinforced opening-containing section of the body could extend rearwardly from the distal end of the body, or be disposed only in an atrial basket region which is spaced rearwardly from the distal end.

BRIEF DESCRIPTION OF THE DRAWINGS

The objects and advantages of the invention will become apparent from the following detailed description of a preferred embodiment thereof in connection with the accompanying drawings in which like numerals designate like elements and in which.

DETAILED DESCRIPTION OF PREFERRED EMBODIMENTS

Figure 1:
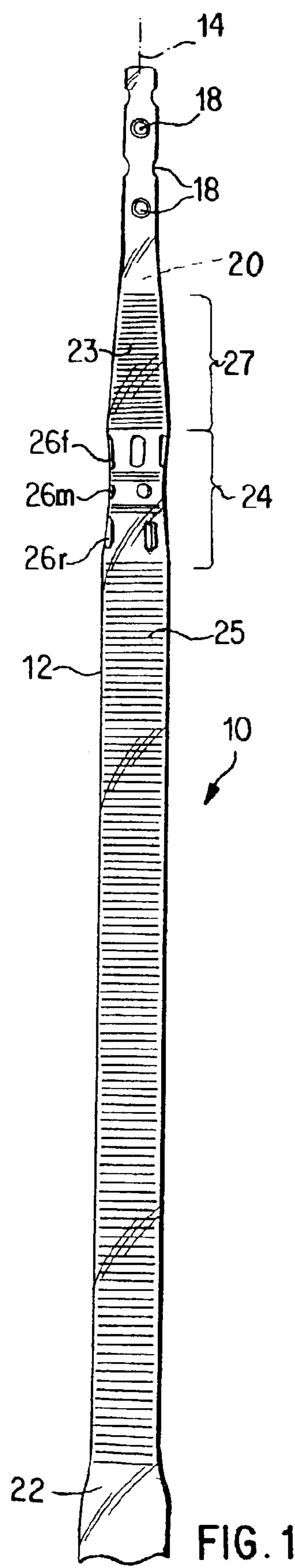
FIG. 1 is a schematic side view of a first embodiment of a catheter according to the present invention.

The present invention is applicable to flexible venous drainage catheters having drainage openings formed therein which communicate with a central lumen for draining blood from a patient.

For example, depicted in FIGS. 1–5 is a two-stage venous catheter 10 comprised of a highly flexible tubular body 12 defining a longitudinal center axis 14. At its forward or distal end, the body is provided with distal drainage openings 18 which communicate with an interior lumen of the body in a radial direction with reference to the axis 14. At a rear or proximal end 22 of the body, the lumen is open in an axial direction for connection with external heart lung equipment.

Front and rear elongated main helical reinforcing coils 23, 25 are embedded in the body 12 on opposite sides of an atrial basket region 24 of the body, in a conventional way. The atrial basket region 24 constitutes a reinforced opening-containing section of the catheter body. Formed in the atrial basket region 24 is a series of drainage openings which extend radially into communication with the lumen 20. The size, number, shape, and relative location of those openings can vary. Depicted are front elongated drainage openings *26f*, rear elongated drainage openings *26r*, and circular intermediate drainage openings *26m*.

During use of the catheter, the distal end section is positioned in the inferior vena cava of the heart, and the atrial basket region 24 is positioned in the right atrium of the heart. Thus, blood is drained from the inferior vena cava through the distal openings 18 and the lumen 20, and blood from the right atrium is drained through the openings 26*f*, 26*m*, 26*r* and the lumen 20.

Figure 2:
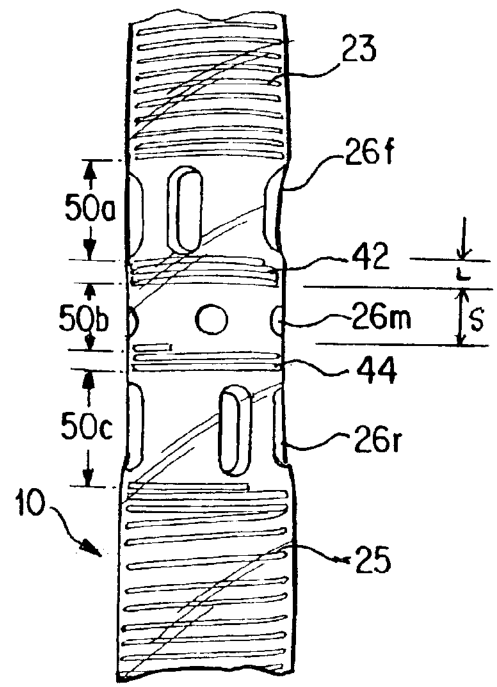
FIG. 2 is an enlarged fragmentary view of an atrial basket region of the catheter shown in FIG. 1.
Figure 3:
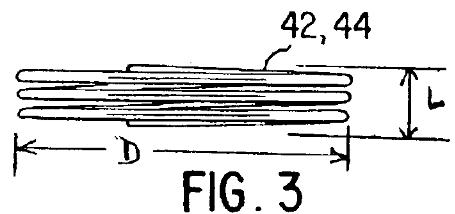
FIG. 3 is a side view of a reinforcing element employed in the atrial basket region according to the invention.
Figure 4:
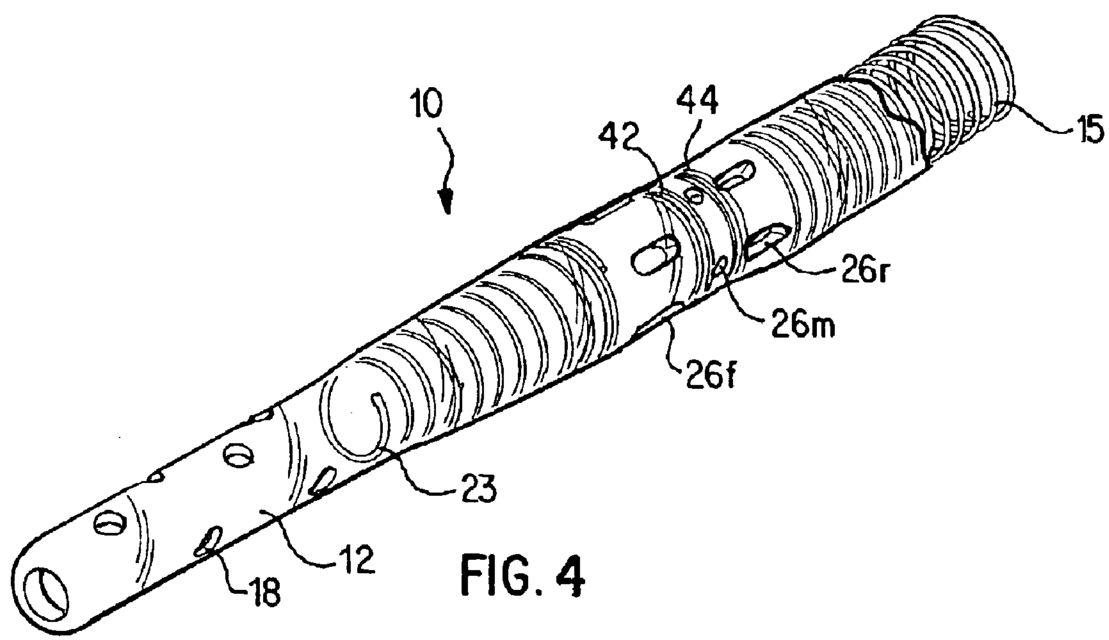
FIG. 4 is a perspective view of a distal region of the catheter depicted in claim 1, with a portion of the catheter body behind an atrial basket region being broken away.

In order to resist kinking as the catheter is being bent while maneuvered into position, the catheter is provided with flexible reinforcement. That reinforcement includes: the front main coil 23 positioned in front of the atrial basket region 24 in a transition region 27 of the catheter, the rear main metal coil 25 situated behind the atrial basket 24, and an atrial basket reinforcement to be discussed. The front main coil 23 gradually increases in diameter toward the atrial basket region 24, whereas the rear main coil 25 is of uniform diameter. As can be seen in FIG. 3, the turns are closely wound, and as can be seen in FIG. 2, the annular members are oriented substantially perpendicularly to a longitudinal center axis of the catheter body. No part of the reinforcement interconnects the annular members, as is also apparent from FIG. 2.

The atrial basket reinforcement comprises a pair of separate annular elements, or ringlets, 42, 44 each of which has an outer diameter D and a very short length dimension L in the axial direction of the catheter. The diameter D is substantially longer than the length as can be seen in FIG. 3. Also, an axial spacing S between adjacent annular elements is greater than the length L as can be viewed in FIG. 2. The ringlets 42, 44 are spaced axially apart from one another along the axis 14 and are spaced axially from each of the front and rear main reinforcing coils 23, 25 (see FIG. 3). Each of the annular elements 42, 44 is preferably in the form a helical metal coil which comprises at least one helical turn, but no more than a few closely wound helical turns, e.g. fewer than five turns, preferably about two and one-half turns. No portion of the ringlets 42, 44 extends parallel to the center longitudinal axis of the catheter, as is evident from FIG. 3.

The atrial basket region 24 is thus subdivided in the axial direction into no fewer than three axially spaced sections, i.e. a front section 50*a*, an intermediate section 50*b*, and a rear section 50*c* (see FIG. 2). An annular row of openings is formed in each of those sections 50*a–c*. That is, a row of the circumferentially spaced openings 26*f* is formed through the body in the front section 50*a*, each of which openings 26*f* being elongated in the axial direction of the body. A row of the circumferentially spaced openings 26*m* is formed through the body in the intermediate section 50*b*. A row of the circumferentially spaced openings 26*r* is formed through the body in the rear section 50*c*, the openings 26*r* being elongated in the axial direction of the body. The opening 26*f*, 26*m*, 26*r* can be of any size and shape (e.g., circular, oval, triangular, etc.) and in any combination of sizes and shapes.

Figure 5:
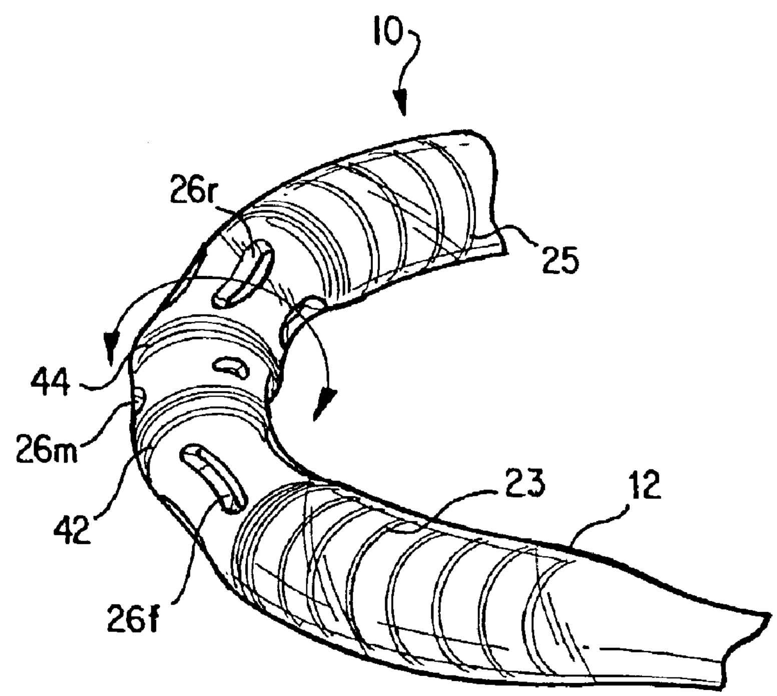
FIG. 5 is a view of the catheter of FIG. 4 being bent in the atrial basket region.

It will be appreciated that the spacing of the ringlets 42, 44 from one another in the axial direction of the body means that the sections 50*a*, 50*b*, 50*c* will be non-reinforced and thus capable of freely bending according to the flexibility of the body itself (see FIG. 5). Thus, the atrial basket is provided with minimal reinforcement, i.e. reinforcement occurs only at axially spaced points. The rest of the atrial basket is non-reinforced and capable of free, uninhibited bending. There is thus no continuous resistance to bending along the entire atrial basket as occurs in the above-described U.S. Pat. Nos. 4,639,252; 5,769,828; and 6,152,911, which resistance limits the maximum bending angle. The catheter 10 functions to drain blood from the inferior vena cava and the superior vena cava of a patient's heart, as described earlier, except that the catheter is able to bend, without kinking, in the atrial basket 24, to a greater extent than the above-described patents.

The ringlets 42, 44 are embedded in the plastic material of the body 12 (e.g., plastisol, or polyvinylchloride, etc.). The manner of embedding the ringlets 42, 44 can be the same as that used to embed the reinforcement in the three above-mentioned patents, the disclosures of which are incorporated by reference herein. That is, a mandrel-and-drip process can be used wherein a mandrel is first dipped in liquified plastic material. Then, the main coils 23, 25 and the ringlets 42, 44 are disposed around the plastic, whereafter the mandrel is re-dipped to embed the coils in the body 12.

The ringlets 42, 44 need not comprise helical coils. Rather, they could comprise other types of annular members, such as rigid circular rings, although coils are preferred.

In accordance with the invention, the problem involving the atrial basket being inadequately bendable is avoided, while ensuring that the atrial basket cannot bend to such an extent that kinking occurs.

Figure 6:
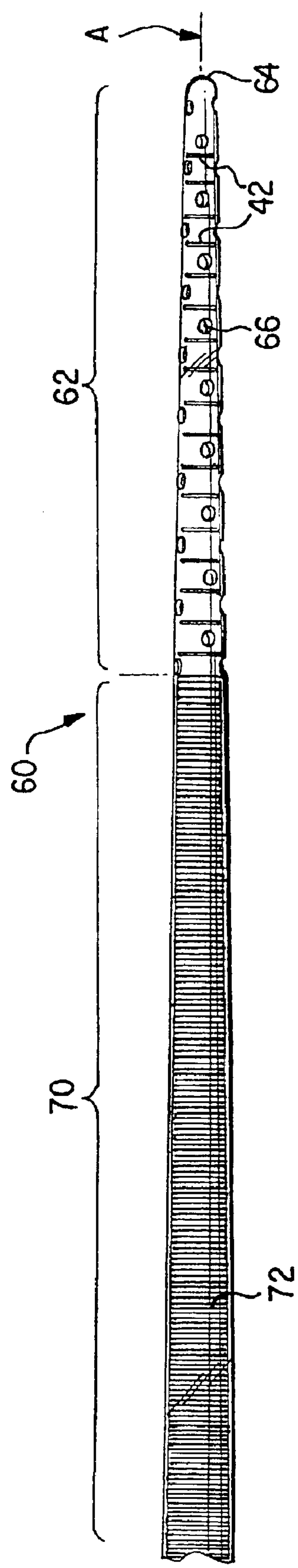
FIG. 6 is a side elevational view of a second embodiment of a catheter according to the invention.
Figure 7:
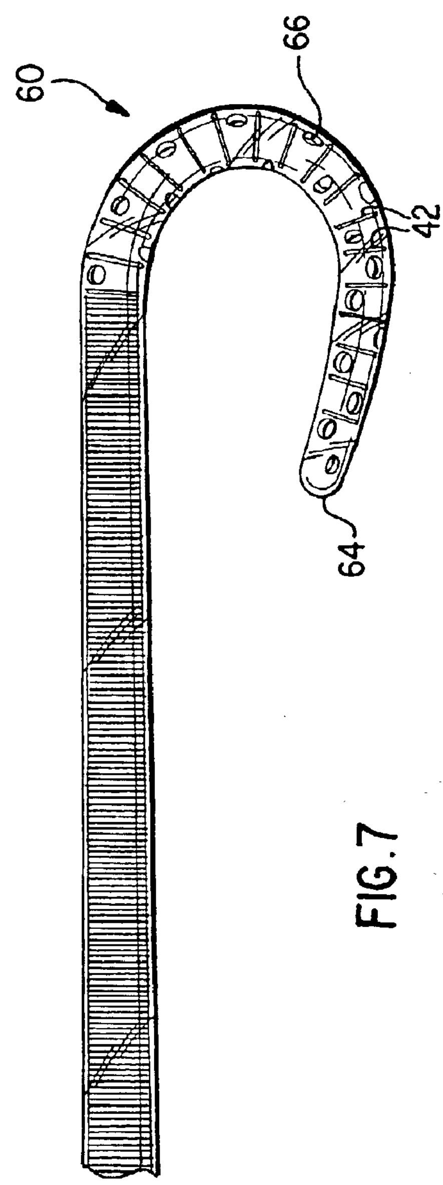
FIG. 7 is a view similar to FIG. 6 after a distal region of the catheter has been bent.

Depicted in FIGS. 6 and 7 is an embodiment of a catheter 60 wherein rather than having an elongated main helical coil separating the openings of the atrial basket region from the openings of the distal region of the catheter, there is provided a single drainage section 62 which encompasses both of those regions. Thus, a reinforced distal section 62 extends rearwardly from the open distal end 64 and includes a plurality of axially spaced openings 66 which are separated by respective axially spaced ringlets 42 that are identical to those described in connection with FIGS. 1–5. Disposed in each space defined between adjacent pairs of the ringlets 42 is a number of circumferentially spaced ones of the openings 66. A portion 70 of the catheter disposed rearwardly of the distal section 62 is reinforced by coil spring 72.

Depicted in FIG. 7 is the manner in which the distal section 60 can be bent rearwardly by about 180 degrees, due to the flexure freedom provided by the annular elements 42.

Figure 8:
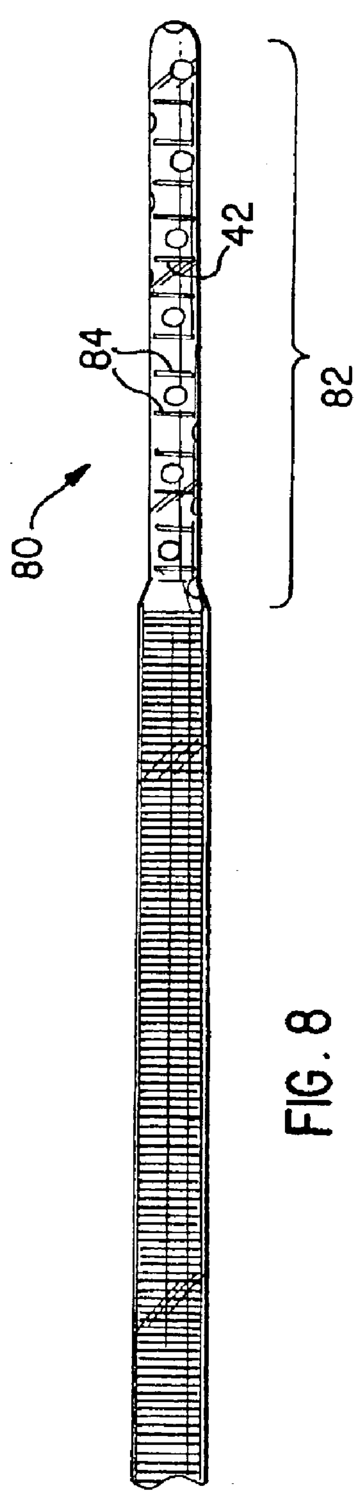
FIG. 8 is a side elevational view of a front fragment of a third embodiment of a catheter according to the invention.

The distal section 60 is shown as being of forwardly tapering shape, wherein the ringlets 42 are of progressively diminishing diameter in the forward direction. However, instead of being tapered, the distal section could be of constant diameter, i.e., cylindrical as shown in another embodiment of a catheter 80 depicted in FIG. 8. In the catheter 80, the distal section 82 in which the drainage openings are formed is of somewhat shorter length than that of FIGS. 6–7, and has a cylindrical shape.

Figure 9:
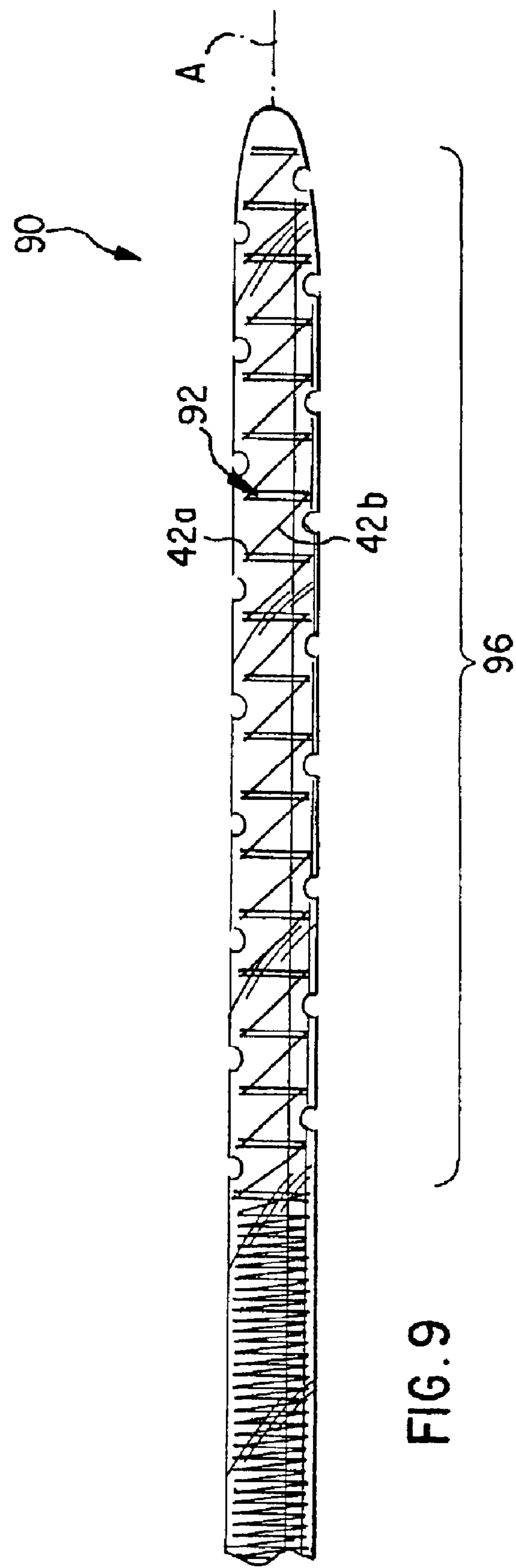
FIG. 9 is a side elevational view of a front fragment of a fourth embodiment of a catheter according to the invention.

In the reinforcement formed by the ringlets 42 of the above-described catheters 10, 60, 80, the ringlets 42 are not interconnected by any portion of the reinforcement. However, in a somewhat modified catheter 90, depicted concept, shown in FIG. 9, adjacent pairs of the ringlets 42*a* are interconnected by connecting portions 42*b* of the reinforcement 92. Preferably the ringlets 42*a* and the connecting portions 42*b* are formed by a continuous wire that is wound by a few turns to form one of the ringlets 42*a* and then continues via the connecting portion 42*b* to form a space and then is wound again to form the next ringlet 42*a*, and so forth. Importantly, the connecting portions 42*b* extend helically relative to the longitudinal axis A of the catheter. Thus, no portion of the reinforcement, including the connecting portions 42*b*, extends parallel to the longitudinal axis A. Each of the connecting portions 42*b* forms an oblique angle with respect to that axis as the catheter is viewed perpendicularly to the axis A. It has been found that the reinforced distal drainage section 96 can be bent rearwardly about as easily as the afore-described catheters 10, 60, and 80, without any appreciable kinking occurring.

Common to each of the catheters 10, 60, 80 and 90 disclosed herein is a reinforced drainage section having reinforcement in the form of a plurality of annular reinforcing elements 42 or 42*a* each arranged perpendicularly to a longitudinal center axis of the catheter, and no portion of the reinforcement extending parallel to the longitudinal axis A.

Although the present invention has been described in connection with a preferred embodiment thereof, it will be appreciated by those skilled in the art that additions, deletions, modifications, and substitutions not specifically described may be made without departing from the spirit and scope of the invention is defined in the appended claims.

What is claimed is:

1. A venous drainage catheter comprising:

a flexible elongated tubular plastic body defining a longitudinal axis and having distal and proximal ends and an interior lumen extending from the distal end to the proximal end along a longitudinal axis of the body, the interior lumen having a plurality of longitudinally spaced drainage openings formed in a reinforced opening-containing section of the body, each opening providing fluid communication between the interior lumen and the exterior of the catheter; and reinforcement embedded in the plastic body within the reinforced opening-containing section, the reinforcement comprising a plurality of annular elements spaced axially apart along the longitudinal axis, each annular element oriented substantially perpendicularly to the longitudinal axis of the body, wherein at least one of the drainage openings is disposed axially between and spaced axially from two adjacent ones of the annular elements, and no portion of the reinforcement interconnects the annular elements;

wherein each annular element defines outer diameter and a length in an axial direction of the catheter, the diameter being substantially greater than the length, wherein an axial spacing between the annular elements is greater than the length of the annular elements.

2. The catheter according to claim 1, wherein each annular element comprises closely wound coils of a wire.

3. The catheter according to claim 2 wherein the reinforcement is formed of metal.

4. The catheter according to claim 1, wherein each annular element comprises a helical coil having no more than five helical turns.

5. The catheter according to claim 1, wherein the catheter comprises a two-stage venous catheter, the opening-containing section of the body defined by an atrial basket region of the body.

6. The catheter according to claim 1, wherein the catheter comprises a multi-stage venous catheter, the reinforced opening-containing section extending rearwardly from the distal end, there being at least ten of the annular elements disposed therein.

7. The catheter according to claim 1 wherein the plurality of annular elements comprises more than two annular elements, with spaces formed between successive ones of the annular elements, at least one of the drainage openings disposed in each space.

8. A venous drainage catheter comprising:

a flexible elongated tubular plastic body defining a longitudinal axis and having a distal end and a proximal end and an interior lumen extending from the distal end to the proximal end along a longitudinal axis of the body, the interior lumen having a plurality of longitudinally spaced drainage openings formed in a reinforced opening-containing section of the body, each opening providing fluid communication between the interior lumen and the exterior of the catheter; and reinforcement embedded in the plastic body within the reinforced opening-containing section and comprising more than two annular elements spaced axially apart along the longitudinal axis to form spaces between successive ones of the annular elements, each annular element oriented substantially perpendicular to the longitudinal axis, wherein at least one of the drainage openings is disposed within each of the spaces and situated axially between and axially from the adjacent annular elements, each annular element comprising a closely wound helical coil, wherein no portion of the reinforcement interconnects the adjacent annular elements, wherein each annular element defines an outer diameter and a length in an axial direction of the catheter, the diameter being substantially greater than the length, wherein an axial spacing between the annular elements is greater than the length of the annular elements.

9. The catheter according to claim 8, wherein each annular element comprises no more than five helical turns.

10. The catheter according to claim 8, wherein the wire is formed of metal.

11. The catheter according to claim 8, wherein the catheter comprises a multi-stage venous catheter, the reinforced opening-containing section extending rearwardly from the distal and, there being at least ten of the annular elements disposed therein.

12. A venous drainage catheter comprising:

a flexible elongated tubular plastic body having a distal end and a proximal end and an interior lumen extending from the distal end to the proximal end along a longitudinal axis of the body, the interior lumen and having a plurality of longitudinally spaced drainage openings formed in a reinforced opening-containing section of the body, each opening providing fluid communication between the interior lumen and the exterior of the catheter; and reinforcement embedded in the plastic body within the reinforced opening-containing section and comprising a continuous wire forming a plurality of interconnected ringlets, each ringlet oriented substantially perpendicular to the longitudinal axis and comprising at least one helical turn, adjacent ones of the ringlets being interconnected by a section of the continuous wire extending helically relative to a longitudinal axis of the catheter, at least one of the drainage openings disposed between and spaced from adjacent ringlets;

wherein each annular element defines an outer diameter and a length in an axial direction of the catheter, the diameter being substantially greater than the length, wherein an axial spacing between the annular elements is greater than the length of the annular elements.

13. The catheter according to claim 12, wherein each ringlet element comprises a plurality of no more than five helical turns.

14. The catheter according to claim 12, wherein the wire is formed of metal.

15. The catheter according to claim 12, wherein the catheter comprises a multi-stage venous catheter, the reinforced opening-containing section extending rearwardly from the distal and, there being at least ten of the ringlets disposed therein.

* * * * *